(12) United States Patent
Marka et al.

(10) Patent No.: US 8,864,038 B2
(45) Date of Patent: Oct. 21, 2014

(54) SYSTEMS AND METHODS FOR FRAUD PREVENTION, SUPPLY CHAIN TRACKING, SECURE MATERIAL TRACING AND INFORMATION ENCODING USING ISOTOPES AND OTHER MARKERS

(71) Applicant: The Trustees of Columbia University in the City of New York, New York, NY (US)

(72) Inventors: Szabolcs Marka, New York, NY (US); Zsuzsanna Marka, New York, NY (US); Imre Bartos, New York, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 55 days.

(21) Appl. No.: 13/681,176

(22) Filed: Nov. 19, 2012

(65) Prior Publication Data
US 2013/0299591 A1    Nov. 14, 2013

Related U.S. Application Data (60) Provisional application No. 61/560,944, filed on Nov. 17, 2011, provisional application No. 61/608,021, filed on Mar. 7, 2012.

(51) Int. Cl.
| | | |
|---|---|---|
| G06K 19/06 | (2006.01) | |
| G06K 19/00 | (2006.01) | |
| G06K 1/12 | (2006.01) | |
| G01N 33/28 | (2006.01) | |

(52) U.S. Cl.
CPC ............... *G06K 19/00* (2013.01); *G06K 1/126* (2013.01); *G01N 33/2882* (2013.01)
USPC ........................................................ 235/491

(58) Field of Classification Search
USPC ........................................... 235/491, 487, 375
See application file for complete search history.

(56) References Cited

U.S. PATENT DOCUMENTS

| | | | |
|---|---|---|---|
| 6,616,051 B1 * | 9/2003 | Zidon | 235/487 |
| 7,143,289 B2 | 11/2006 | Denning et al. | |
| 7,660,418 B2 | 2/2010 | Glick et al. | |
| 8,009,034 B2 | 8/2011 | Dobson et al. | |
| 8,022,573 B2 | 9/2011 | Powers et al. | |
| 8,102,256 B2 | 1/2012 | Scalisi et al. | |
| 8,103,056 B2 | 1/2012 | Krishnaswamy et al. | |
| 2010/0102250 A1 * | 4/2010 | Li et al. | 250/459.1 |
| 2011/0305919 A1 | 12/2011 | Conroy et al. | |

OTHER PUBLICATIONS

Al-Fuqaha, et al., "Geo-Encryption Protocol for Mobile Networks", *Computer Communications*, 30(11-12):2510-2517 (2007).

(Continued)

*Primary Examiner* — Christle I Marshall
(74) *Attorney, Agent, or Firm* — Baker Botts LLP (57) ABSTRACT

Encoding information in a material using a material tracing system includes storing information to be encoded in the material, generating a number based on the information, determining an amount of at least one tracer to be incorporated into the material corresponding to the number, and incorporating the determined amount of the at least one tracer into the material. Decoding information encoded in the material includes measuring an amount of the at least one tracer, in some embodiments after tracer activation, determining a number corresponding to the measured at least one tracer, and decoding the number to obtain information associated with the material. A material tracing system is also provided.

19 Claims, 3 Drawing Sheets

(56) References Cited

OTHER PUBLICATIONS

Elango, et al., "Indoor TMD Secure System for Early Detection of Alzheimer's Disease", *Advanced Materials Research*, 433-440:2237-2243 (2012).

Hamad, et al., "Data Encryption Using the Dynamic Location and Speed of Mobile Node", *Journal Media and Communication Studies*, 2(3):067-075 (2010).

Liao, et al., "A New Data Encryption Algorithm Based on the Location of Mobile Users", *Information Technology Journal*, 7(I):63-69 (2008).

Reddy, et al., "Data encryption Technique Using Location Based Key Dependent Permutation and Circular Rotation", *International Journal of Computer and Network Security*, 2(3):46-49 (2010).

Yan, et al., "A Geographic Location-Based Security Mechanism for Intelligent Vehicular Networks", *Intelligent Computing and Information Science, Communications in Computer and Information Science*, 135:693-698 (2011).

\* cited by examiner

FIG. 1

Neutron activation analysis, also nondestructive, in addition enables volume measurement.

Nondestructive tracing method examples

FIG. 2

Neutron-activation analysis (NAA) can differentiate between nuclear isotopes. Such isotopes are chemically identical and are extremely difficult to distinguish with other techniques.

SYSTEMS AND METHODS FOR FRAUD PREVENTION, SUPPLY CHAIN TRACKING, SECURE MATERIAL TRACING AND INFORMATION ENCODING USING ISOTOPES AND OTHER MARKERS

CROSS-REFERENCE TO RELATED APPLICATIONS

This application claims priority to U.S. Provisional Patent Application Ser. No. 61/560,944, filed on Nov. 17, 2011 and U.S. Provisional Patent Application Ser. No. 61/608,021, filed on Mar. 7, 2012, each of which is incorporated by reference herein in its entirety.

BACKGROUND

The disclosed subject matter relates to systems and methods for fraud prevention, supply-chain tracking, secure material, object or organism tracing and information encoding (collectively referred to as "trace element encoding" or "tracing").

Marking valuable items, which can include liquids, gases, solids, gels, crystals, quasi-crystals, metals, alloys, other raw materials, plastics, mechanical parts, fuel, medicines, food, drinks, or any other suitable materials, can facilitate identification, authentication, fraud prevention, supply-chain tracking of the items. Various techniques to identify, trace, track, age, mark, serially number, or otherwise label valuable items and/or stocks of items can be utilized. For example, marking of solid items can involve applying a physical label, such as a stamp, tag, etching, plaque or the like, which can include relevant information about the origin of the item, such as the logo of the manufacturer, serial number, date of production and place of origin. However, such physical labels can be relatively easily forged or removed, and can contain limited information about the item. As such, counterfeit items can be made to appear as genuine valuable items, and this illegal practice can have a negative economic impact on producers and consumers of genuine items.

Marking valuable items in the form of a liquid or gas, including perfume, industrial supplies, gasoline or natural gas, can involve adding visible and/or scented dyes to the item. However, such dyes can be obtained and utilized or removed by counterfeiters, can devalue the product, and also can include relatively limited information about the origin of the item. Furthermore, manufacturing such dyes typically utilizes complex machinery, which can result in centralized production and distribution of the dyes. As such, modification of coded information in dyes can be difficult, and encoding each product individually can also be challenging.

Therefore, there remains an opportunity for systems and methods for marking valuable items that are secure, permanent, difficult to forge, traceable, easy to modify, can be unique to individual products, and can include a large amount information about the item and its components.

SUMMARY

Systems and methods for fraud prevention, supply-chain tracking, secure material tracing and information encoding (collectively referred to as "trace element encoding" or "tracing") are disclosed herein.

The disclosed subject matter provides systems and methods for material tracing. In an exemplary embodiment, a method for encoding information in a material includes storing information to be encoded in the material, generating a number based on the information, determining an amount of at least one tracer to be incorporated into the material corresponding to the number, and incorporating the determined amount of the at least one tracer into the material.

In some embodiments, the at least one tracer includes a plurality of trace elements, each trace element corresponding to one of a plurality of bits of the number, and the method further includes arranging the plurality of trace elements in an order corresponding to the order of the plurality of bits of the number. In some embodiments, the number includes a binary number and the amount of each of the plurality of trace elements includes a first amount corresponding to a '1' bit of the binary number or a second amount corresponding to a '0' bit of the binary number, and determining the amount of the at least one tracer includes, for each trace element, determining whether to incorporate the first amount of the trace element or the second amount of the trace element corresponding to the binary number. The number can include a 64-bit binary number and the at least one tracer can include 64 trace elements, each trace element corresponding to a bit of the 64-bit binary number.

In some embodiments, the at least one tracer includes one or more stable elements. Additionally or alternatively, the at least one tracer can include one or more radioactive elements. A total radioactivity of the one or more radioactive elements can less than or equal to 0.4 counts per second. Furthermore, the at least one tracer can include one or more non-radioactive elements that becomes radioactive upon activation, and the method can further include activating the one or more elements, which can include applying neutron irradiation or gamma irradiation to the one or more elements.

In some embodiments, the information can include one or more of an age, purity, manufacturer, marking or serial number of the material.

According to another aspect of the disclosed subject matter, a method for decoding information encoded in a material with at least one tracer incorporated into the material includes measuring an amount of the at least one tracer using a measuring device, determining a number corresponding to the measured at least one tracer based, at least in part, on the measured amount of the at least one tracer, and decoding the number to obtain information associated with the material.

In some embodiments, measuring the amount of the at least one tracer comprises measuring one or more stable elements using x-ray fluorescence (XRF), neutron activation analysis (NAA), particle-induced x-ray emission (PIXE) or any other suitable analytical method. Additionally or alternatively, measuring the amount of the at least one tracer can include measuring one or more radioactive elements using a gamma spectrometer. Furthermore, measuring the amount of the at least one tracer can include activating the one or more elements by neutron irradiation or gamma irradiation.

According to another aspect of the disclosed subject matter, a material tracing system includes one or more processors, one or more computer readable storage media, and a measuring device in communication with the computer readable storage medium.

DETAILED DESCRIPTION

The disclosed subject matter provides systems and methods for fraud prevention, supply-chain tracking, secure material tracing and information encoding (collectively referred to as "trace element encoding" or "tracing"). The disclosed subject matter is not limited to the materials described herein, and can be suitable for a broad range of materials. For example, the disclosed subject matter can be used for tracing liquids, gases, solids, gels, crystals, quasi-crystals, metals, other raw materials, plastic, medical tools and medicine, food, drinks, alloys, or any other suitable materials. The disclosed subject matter can be used to trace specific products individually, groups of items collectively or batches of bulk items or material as a single unit.

An exemplary embodiment according to the disclosed subject matter can include material tracing using rare material markers. Another exemplary embodiment can include material tracing using rare and controlled radioactive markers. Yet another exemplary embodiment can include activation of hidden contaminants. The exemplary embodiments described herein can be utilized alone or in combination, and thus can be complementary while providing varying layers of security.

Physically and cryptographically strong encoding of information within a material itself at production can reduce the chance of tempering or misusing a precious metal stock and the added expense associated with purity, owner, and tax-related identification of the stock. Electronics security industries can rely on 64-bit encoding to prevent unique codes to devices from being repeated and enable relatively strong cryptography and encoding of user information, such as global markers and serial numbering. Such encoding can provide $2^{64}$ distinct combinations, which can be suitable for material tracing. Nevertheless, the systems and methods disclosed herein can readily be generalized, for example, to 64-bit content, or any other suitable content depending on the application. The embodiments below refer to the number 64 and to 64-bit encoding as an example and for purposes of illustration and not limitation; however, a wide range of numbers of bits can be utilized within the scope of the disclosed subject matter. For example, some embodiments can utilize about 8-10 bits.

Figure 1:
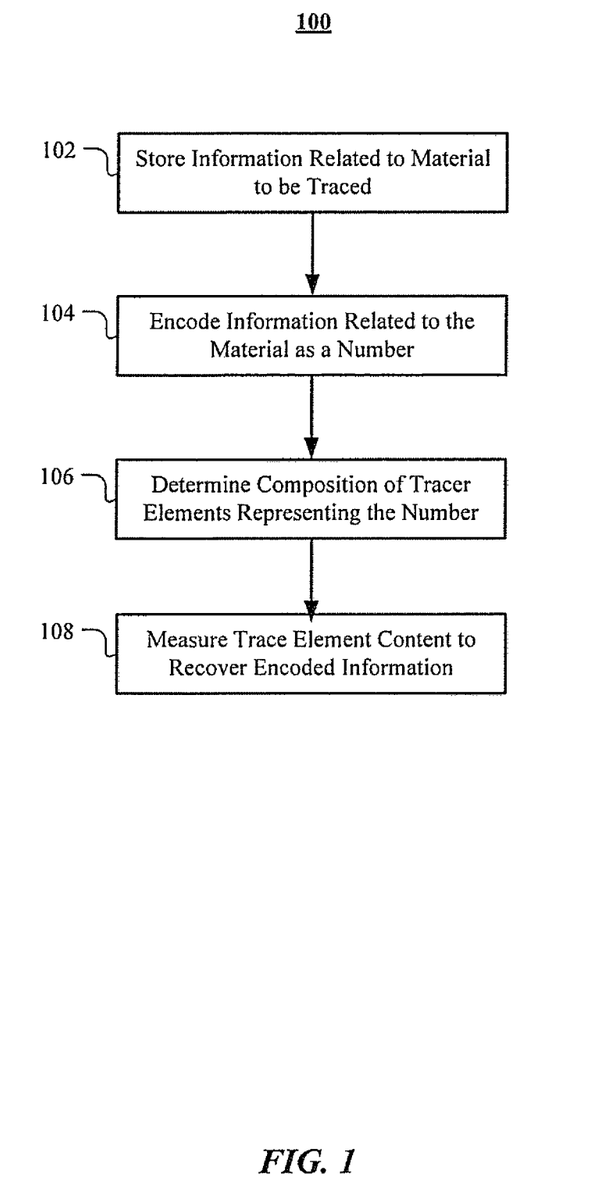
FIG. 1 illustrates an exemplary technique for material tracing according to the disclosed subject matter.

FIG. 1 illustrates an exemplary technique 100 for material tracing according to the disclosed subject matter. At 102, information related to a material to be traced can be stored in a computer readable storage medium, for example in a database. In this manner, a library of marked and traceable objects can be created for future reference and for precise identification of traced objects.

At 104, the information related to the material can be coded, for example by generating a number corresponding to the information. The number can be associated with the information related to the material in the computer readable storage medium. Additionally or alternatively, the number can be a direct representation of a meaningful number, such as a serial number or date of manufacture, or a cryptographically secured representation of the meaningful number. For example and without limitation, as described herein, the number can be represented as a binary number. However, any base of number can be utilized in accordance with the disclosed subject matter.

Furthermore, information can be encoded according to the disclosed subject matter within the bulk and the surface of the material, which can be later recovered, for example as discussed below. The encoded information can change from point to point in 1, 2 or three dimensions (for example, using tape, disk, or cube style storage). The recording medium can be an object (for example, a 3D-printed sculpture where each cubic millimeter can be encoded with different information and the total message can be contained within the entirety of sculpture) or bulk material, such that any sample of the material contains a similar encrypted message. Furthermore, biological material can be grown to include an encrypted message. For example, nutrients can include trace materials that can, upon ingestion, become embedded in biological materials, such as hair, nails, horns, bones, trees or other biological materials, as a function of time. In this manner, the biological materials can become a proxy for "tape" that can be read and decoded, each piece of biological material containing similar information.

At 106, the binary number can be represented as various amounts of trace elements to be incorporated into the material. For example, a discrete number of different trace elements can be added into a material. Each trace element can be added in a predetermined quantity, with some being added in small quantities and some being added in larger quantities. A predetermined order of the trace elements can be defined. The trace element content of the resulting material can be accurately recovered, as described further below. The binary number can be represented such that each bit of the binary number corresponds to an individual trace element added to the material. The order of the bits can correspond to the predetermined order of the trace elements. Each bit in the binary number can be represented as a value of "1" if the content of the trace element is high, and can be represented as value of "0" if the content of the trace element is low. As such, the binary number can serve as a unique marker for a particular piece of material, and can be associated with the information related to the material. Furthermore, the binary number itself can contain encoded information comprising, for example, age, purity, manufacturer, date of manufacture, marking, serial number, and/or a number of different attributes of the stock of material.

Different isotopes of the same element can also be used as trace markers, and to increase security can be used at an altered concentration ratio compared to a naturally occurring one. For example, rubidium (Rb), which has one stable and one slightly radioactive naturally occurring isotope, can be useful as a trace element.

The composition of the tracer elements corresponding to the binary number can be stored in the computer readable medium for future reference and identification of traced objects. Furthermore, a fraction of each composition of tracer elements can be preserved at the cryptographic center before shipping it to the manufacturer. The compositions can be filed into a physical data base to complement the cryptographic data base. Indeed, marker compositions can be difficult to detect without a priori knowledge of the composition information.

In some embodiments, once a combination of trace elements is determined, the trace elements can be combined, for example in the form of a pellet, which can be inserted into an item or added to a stock of bulk material during manufacturing. The pellet can be formed using a pellet fabricator, which can be, for example and without limitation, any suitable device for forming a pellet-shaped compound, such as a pharmaceutical pill or the like. The pellet fabricator can receive the composition information for the pellet from the one or more processors used to determine the composition of trace elements, as described above.

In some embodiments, a protected item can be marked multiple times during the manufacturing process. For example, metals or other materials used to fabricate the item can be marked following their purification or melting, while the final product can be marked one or more additional times during the assembly. Such marks can facilitate the tracking of the manufacturing process, and can provide independent, distinct and distinctly recoverable information about the final product.

For example and not limitation, the number of different trace elements can be 64. The use of 64 different trace elements can ensure unique markers for different stocks. Any number of different trace elements can be used, and the number of different trace elements can be varied to suit an intended purpose.

In one embodiment, the trace elements added to a material include different stable rare elements, where the rare elements are not natural contaminants of the material. At 108, the trace element content can thereafter be accurately recovered in standard laboratories to construct the binary number including the trace elements, for example using x-ray fluorescence (XRF), neutron activation analysis (NAA), particle-induced x-ray emission (PIXE) or any other suitable analytical method.

In another embodiment, the trace elements can be rare and controlled radioactive markers. For example, the trace elements can be different gamma emitting radioisotopes that are not contaminants of the material. At 108, a gamma spectrometer, cesium iodide (CsI)-based detector or other suitable detection device can be used to accurately identify radioisotope content without sampling or removal of the stock from its storage. The binary number can thus be constructed based on the concentration of the different radioactive markers. The natural decay of radioisotopes can also enable the precise dating of the creation of the stock.

Information content encoded with radioisotopes can be limited by limitations on emission flux. Greater emission can allow for greater resolution in assigning information to different levels of emission, given a limited measurement duration. Limitations on emission flux can be estimated to reduce health concerns.

Background radiation on Earth generally is about 2 mSv/year. Safety limits of man-made facilities can be 1 mSv/year. For a gamma radiation energy of 1 MeV, the safety limit can correspond to about 200 counts/sec. However, background radiation can also be in the form of alpha and beta radiations.

To increase safety, even in the vicinity of relatively large amounts of tracked material, a safety limit can be provided, for example of 1000× below what 1 kg of tissue receives from background radiation for a tracked material with the weight of a gold bar (i.e., 400 troy ounces=12.4 kg). If a radiating source deposits 50% of its energy in 1 kg of tissue while someone is standing proximate to it, the limitation can be 0.4 counts/sec/gold bar. Heavy elements, such as gold or other precious metals, can relatively quickly attenuate gamma-rays with a half length of less than about 2 cm, and thus the radiation from a relatively smaller piece of jewelry of the precious metal can be greater than that obtained from comparing its mass to the mass of a gold bar.

If photons leaving the gold bar can be detected, with about 0.4 counts/sec/gold bar emission, whether the gold bar has the radioisotope tracer or not can be determined in about 4.61/0.4=11.5 seconds, with about 99% probability, (or about 5.75 seconds for about 90% probability). Thus, relatively quick and accurate determination of the presence of the tracer can be followed up with a relatively longer information extraction time. The amount of tracing material present can also be decreased with an even longer information extraction time.

Figure 2:
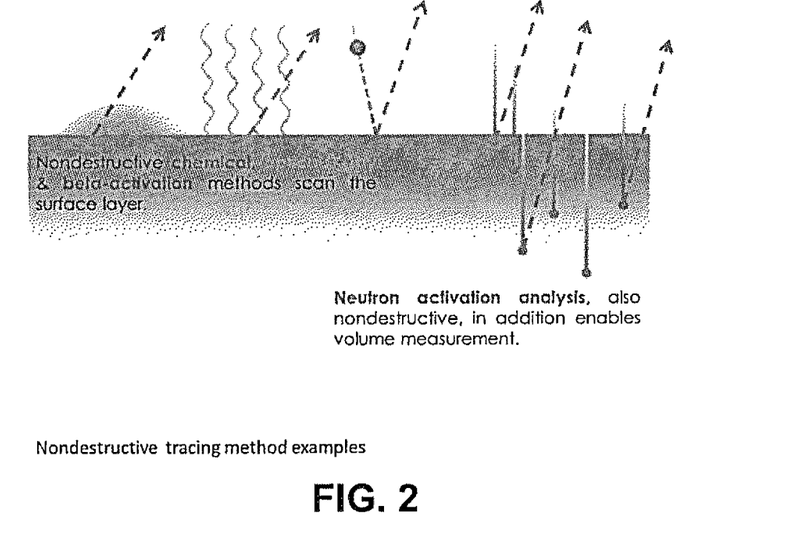
FIG. 2 illustrates further details of the technique of FIG. 1.
Figure 3:
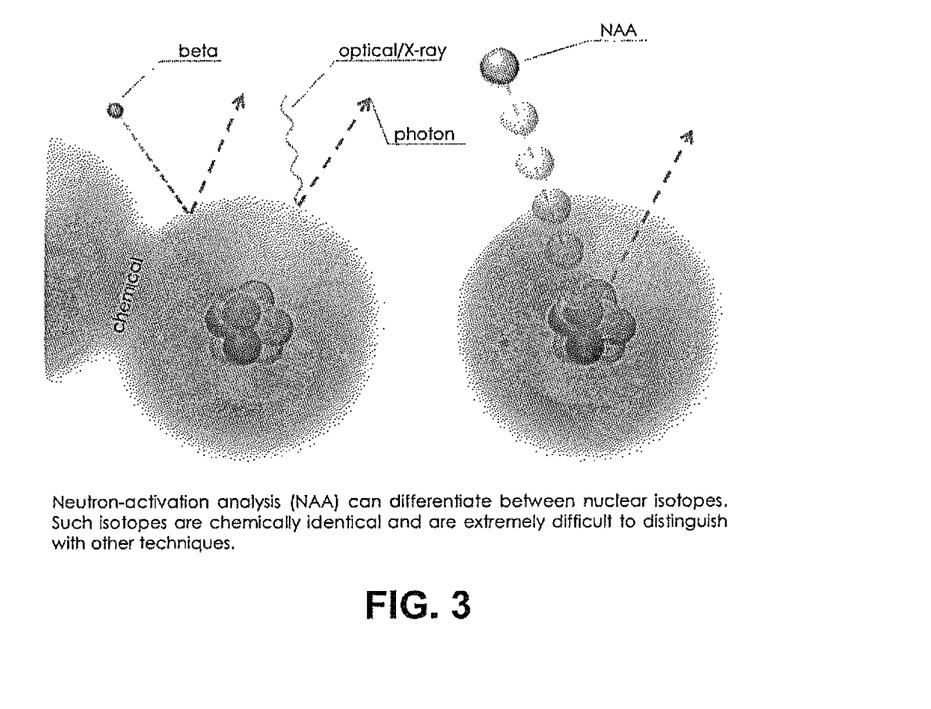
FIG. 3 illustrates further details of the technique of FIG. 1.

In another embodiment, the trace elements can be hidden contaminants. For example, the trace elements can be materials that are normally non-radioactive but become temporarily radioactive upon neutron irradiation or by other means. As illustrated in FIG. 2, the material stock can be irradiated, whereby the added contaminants are converted into short lifetime radioactive isotopes. For example, nondestructive chemical, optical/X-ray and/or beta-activation techniques, such as X-ray fluorescence (XRF), can be utilized to scan the surface layer of the material, and neutron activation, or other nuclear methods can be used to activate the trace elements embedded in the volume of the material to uncover the embedded information. As such, at 108, the response of the activated trace elements can be measured and used to construct the binary number. Furthermore, neutron-activation analysis (NAA) can be utilized to obtain a volume measurement, and can also be used to differentiate between nuclear isotopes, as shown in FIG. 3. NAA can be performed after neutron irradiation from, for example, nuclear reactors, neutron generators, various accelerators, Am—Be or Pu—Be or other sources capable of providing neutron flux. The nuclear isotopes can be substantially identical chemically, and thus can be difficult to distinguish using other techniques.

Furthermore, trace elements can have time dependent quantities or quantity ratios, for example elements or substances that contain the elements that can decay at various rates due to chemical or nuclear decay, which can be used to measure a time from manufacturing or any other point in their lifecycle as the initially embedded quantities and material quantity ratios can change in a statistically predictable way with passing time. In this manner, NAA, gamma spectrometry or any other suitable analytical method can be used to recover the age and the time intervals encoded in the material between analyses.

In one example, a mixture of trace elements, including Ca, Zn and Fe in small quantities were embedded in an approximately 6 mm×6 mm×1.3 cm human digestible matrix (for example, Centrum Silver 50+ Multivitamin by WYETH, White Hall Export GmbH, 1 Storchengasse, Vienna A-1150, Austria, S#:0TS185). The amounts of the trace elements in the material were identified using NAA and XRF to obtain information about the trace elements present in the sample and were confirmed by comparison to the manufacturer's composition specifications.

In yet another embodiment, rare material markers, rare and controlled radioactive markers, the addition of hidden contaminants, naturally-occurring elements and other information channels can be used in combination. Coding information can be achieved with tracers together with other information channels. For example, 64-bit (cryptographic) coding can be achieved by using N tracer elements in a binary setting and placing the remaining (64−N) bits on the product or by correlating it in some other way to the product. For example, a medication can have different 5-bit coding in the form of 5 tracer elements within each individual pill, tablet, or capsule, while the remaining 59 bits of information can be placed on the package. With the proper encryption, the total 64 bits of information can be read by someone in possession of, for example, a private key to decode the information. Such techniques can allow each pill, tablet, capsule, or other encoded material or item to store relatively large amounts of encrypted information, and thus their authenticity can be determined.

In some embodiments, trace elements can be used in combination with conventional encoders, such as bar codes, surface marks, shaping and the like. The information stored about the item can be distributed and encrypted such that the information can be deciphered by recovering the information from all of the components. In this manner, each trace element can represent more than one bit of information, and the amount of information stored can be increased while using less trace elements.

The amount of information stored can be increased by using two or more sets of tracer elements. One set of tracers can be used as a comparison tracer, and the quantity of the other tracer elements can be set compared to the comparison tracer following a coding scheme, for example by having 1/n, 2/n, 3/n, . . . 1 fractions of the comparison tracer. Activation details of secure tracer elements can also be included in a secure encryption scheme, such as the neutron energy and irradiation duration per tracer isotope.

Various levels of information can be stored using different types of tracer elements, which can increase reliability and security. For example, manufacturer, origin and date can be encoded using stable tracer elements, while confidential manufacturer information can be encoded using tracer elements that can be activated. Additionally, resellers can use some embodiments to include additional layers of information, while governments could rely on some embodiments for export control, security and tax evasion investigations, for example.

In another aspect of the presently disclosed subject matter, the binary number constructed from the material can serve to identify a material stock that has been tampered with. That is, if a stock has been tampered with, the binary number constructed will be altered, and thus it can be determined that the stock is not genuine. For example, if one mixes a traced stock of material with a non-traced stock, the binary number will not decode properly. In addition to measuring the trace element content of each different trace element, the overall concentration of trace elements can be measured to determine whether pure material has been added to the stock.

EXAMPLE

Systems and methods disclosed herein can be used to identify forgery. For example, by melting traced gold and mixing it with non-traced gold, resulting in a percentage of traced gold of X percent, a measurement of a duration of about 1150/X seconds can be used to identify if traced gold was used with about 99% probability. Additionally, even if the traced material makes up only about 10% of the total, the ratio can be identified with about 99% probability within about 2 minutes or less. The same procedure can be utilized for materials other than gold, such as any of the materials described herein.

The time period needed for the extraction of given amount of information from one radioactive tracer from a gold bar can be calculated with a relatively high precision (for example, 99.993%, or $4\sigma$). Information can be stored by changing the level of radiation from zero up to about 0.4 counts/sec in a gold bar (or other suitable material). One tracer component can be considered, and then generalized for multiple components, as discussed further below. For a measurement of duration T, for a gold bar with average radiation of N counts/sec, the average number of detected photons from the gold bar can T*N photons. The measurement error of the average can be $\sigma=\text{sqrt}(T*0.4)$. For $4\sigma$ precision, the number of distinct levels or radiation can be about $T*0.4/4\sigma=\text{sqrt}(T [\text{sec}])*0.16$. For example, for a measurement of 1 hour, the amount of information extracted can be about 3.25 bits. For a 1-day-long measurement, the amount of information can be about 5.5 bits. An information content of 1 bit can be restored with a measurement of about 157 seconds.

One can use multiple tracers to improve the amount of information that can be stored in tracers. For example and without limitation, 4 distinct tracers can be used. While using multiple tracers, the total radiation can be limited to the 0.4 counts/sec limit. One of the 4 distinct tracers can be a standard tracer, that is its radiation level is relatively fixed, for example at ¼th of the total limit or 0.1 counts/sec. And thus, about 4× more time can be used to recover information on the presence of tracing materials (as discussed above). The other 3 of the 4 distinct tracers can have a maximum level of 0.1 counts/sec. For this level of radiation, the amount of information recovered during a measurement of duration T can be $\text{sqrt}(T[\text{sec}])*0.08$. For a 30-minute measurement, about 5 bits of information can be recovered from a given tracer, for a total of about 15 bits for the 3 information bit. Stored information can be increased, if desired.

Information related to the time of the production of the gold bar can be stored in the form of tracing materials. This can utilize a tracer, for example having a half-life on the order of a few years. With such a tracing material, and using the original radiation level, the time elapsed since production can be measured. Such a measurement can be useful to prevent forgery. The presence of a standard radiation source can allow, for example, for the comparison of what percentage the tracked object was diluted, and thus the date of the original production can be recovered.

In addition to identifying fraud, forgery, or theft, the disclosed subject matter can be used to encode information about the material. For example it can be used to trace the spread, transfer, distribution, or dilution of a given material or product, to identify origin, processing, ownership, store information such as production time, place, and other related information. The disclosed subject matter can be used for validation, tracking supply chains, identifying points of theft, contamination, and/or points of loss.

The disclosed subject matter can also be used to (a) track the spread of drugs and other chemicals in living systems or elsewhere; (b) recover the mixing ratio of different alloys, liquids or components; (c) recover a tracer ratio, for example if each component of a mix is marked with a tracer, the alloy or mix of these components can have a tracer ratio that is specific to the ratio of the components in it.

The disclosed subject matter can also be used, for example and without limitation, for (a) tracing of pharmaceuticals, legal and illegal drugs, such as pills, tablets, capsules, liquids, gases, patches, implants, enhancements, etc.; (b) validation of drugs mixed on the spot by a pharmacist or the like, such as creams or IVs; (c) validation of blood supply and other personalized medical items; (d) personal hygiene items, beauty supplies, fragrances, wigs, cosmetic products (e) controlled items, such as kosher goods; (f) books; (g) musical equipment; (h) furniture and furniture material, such as wood or leather; (i) aircraft materials and components; (j) electronic components, such as ICs, processors, chips, capacitors, or any other electronic part; (k) encasing for electronic components, semiconductor materials, wiring insulation, wiring, circuit boards, and other commercial, professional and consumer electronics related items; (l) mission critical or other mechanical parts such as bolts, belts, parts of vehicles, machines, any other contraptions; (m) rated vehicle parts can be identified, validated and traced to ensure reliability and proper usage; (n) the authenticity and/or history of machine/vehicle parts can be labeled and traced such that they cannot be sold separately or the authenticity of a new component can be verified, e.g., to stop chop shops; (o) components, items or material used in buildings, such as concrete or bricks; (p) medical devices and implants; (q) sterile equipment; (r) pieces of art, such as sculptures, paintings, collectibles, and other items of value, for example for use by museums, collectors and others; (s) currency, bills, certificates, bonds, checks, lottery or other tickets, etc.; (t) liquid resources, oil, natural gas, gasoline, diesel, etc.; (u) authentication of food items such as honey, oil, and other bulk products, for example to trace meat or vegetables, e.g. paprika, and relatively high-value drinks, such as whiskeys, or baby formula, can also be traced and authenticated; (v) fashion items—textile, shoes, etc. and other relatively high-value goods subject to counterfeiting; (w) jewelry, pearls, diamonds; (x) living organisms or their remains; (y) military and security equipment; (z) or any other suitable object, material, or composition to be traced.

Additionally, systems and methods disclosed herein can be used by museums, for example for asset tracking, and collectors can mark their validated art investment to protect against various theft schemes.

The disclosed subject matter can be used by tax authorities to track the commerce of traced goods (for example diamonds or precious/rare metals) and verify origin, time of production, or other information, about goods.

The disclosed subject matter can be used to verify to consumers that they are not buying goods produced by unethical entities (for example, blood-gold or blood-diamonds, or products using child or forced labor).

The disclosed subject matter can be used by drug enforcement authorities. For example, drugs can be marked at their production site, after which the tracing can be relatively difficult to remove. Drugs found later in the supply chain can be identified, and connections in drug trafficking can be determined.

The disclosed subject matter can be used for personalized medicine, for example where a relatively large number of different drugs can make authentication relatively difficult and misuse relatively dangerous. The disclosed subject matter can provide relatively quick and easy identification of such medicine, for example for single pills or other components.

The disclosed subject matter can be used for authentication of batteries, which can pose a security risk due to their contents being relatively hard to verify. Tracing batteries can reduce such risks.

The disclosed subject matter can be used for authentication of items of personal hygiene, and thus can prevent such items from being provided by unreliable sources, which can threaten the health of its users.

The disclosed subject matter can be used for authentication of building components. For example, upon marking cement at its origin, the cement content of concrete can be determined, and thus be used to avoid various threats to the safety of the building.

The disclosed subject matter can be used for tracing goods such as oil or natural gas. For example, including a known amount of tracer into these goods can allow the content of sold products at different points of the supply chain to be determined. Further, households can verify whether the natural gas they receive from a provider includes the claimed purity of natural gas. Additionally, leakage of air or CO2 into the received gas can be identified through tracing. Similarly, the components of gasoline can be verified. Further, time-dependent marking of gas or oil in pipelines can be used to determine if turbulent flows arose at given parts of the pipeline through indicating the level of mixing within the liquid. This can be used to reduce the energy needed to transport these liquids within the pipelines.

The disclosed subject matter can be used to facilitate embargos, or other similar restrictions, against bulk producers (for example, producers of oil).

The disclosed subject matter can be used for tracing industrial chemicals, and thus contamination of civilian chemicals or other non-intentional contamination can be identified.

The disclosed subject matter can be used for tracing animal parts, for example trunks and horns of elephants and rhinos, and thus can be identified even in powder form or even if a relatively small portion of the parts is available.

The disclosed subject matter can include devices capable of injecting the tracing materials in predetermined quantities, and devices that can monitor and display the information in the tracers. Injecting and/or reading the tracers can also be provided by a commercial service provider. Additionally, code pellets, droplets, powders, and the like, that include combinations of tracing material can be deposited, and thus can reduce machine costs on-site.

The disclosed subject matter can allow for tracing or detection of illegal and legal performance enhancing drugs.

The disclosed subject matter can be used for coding plastic items by inclusion of a code pellet containing the tracing material before mixing, and thus production costs can be reduced from not using on-site coding hardware.

The disclosed subject matter can be used for tracing food-quality items and non-food-quality items, and thus food-quality items can be labeled and distinguished from non-food-quality items.

The disclosed subject matter can be used for tracing and/or labeling endangered items, such as endangered tropical hardwood, endangered species, or other endangered living organisms, such as ivory, rhino horn and tigers.

The disclosed subject matter can be used for tracing light sources, such as bulbs, which can include tracer materials. Residual emission/absorption lines in the spectrum due to tracing materials can allow for identification of a lamp or can encode other information.

The disclosed subject matter can be used to securely identify electronics parts as genuine and untampered in a destructive or non-destructive way, and can leave the parts reusable. Physical component (for example, gold wiring, epoxy, silicon, solder joints, etc.) can similarly be traced, for example components of integrated circuit chips within their 3D entirety from point to point, which can be used to ensure component is bona fide and no extra components have been implanted inside the part.

Figure 4:
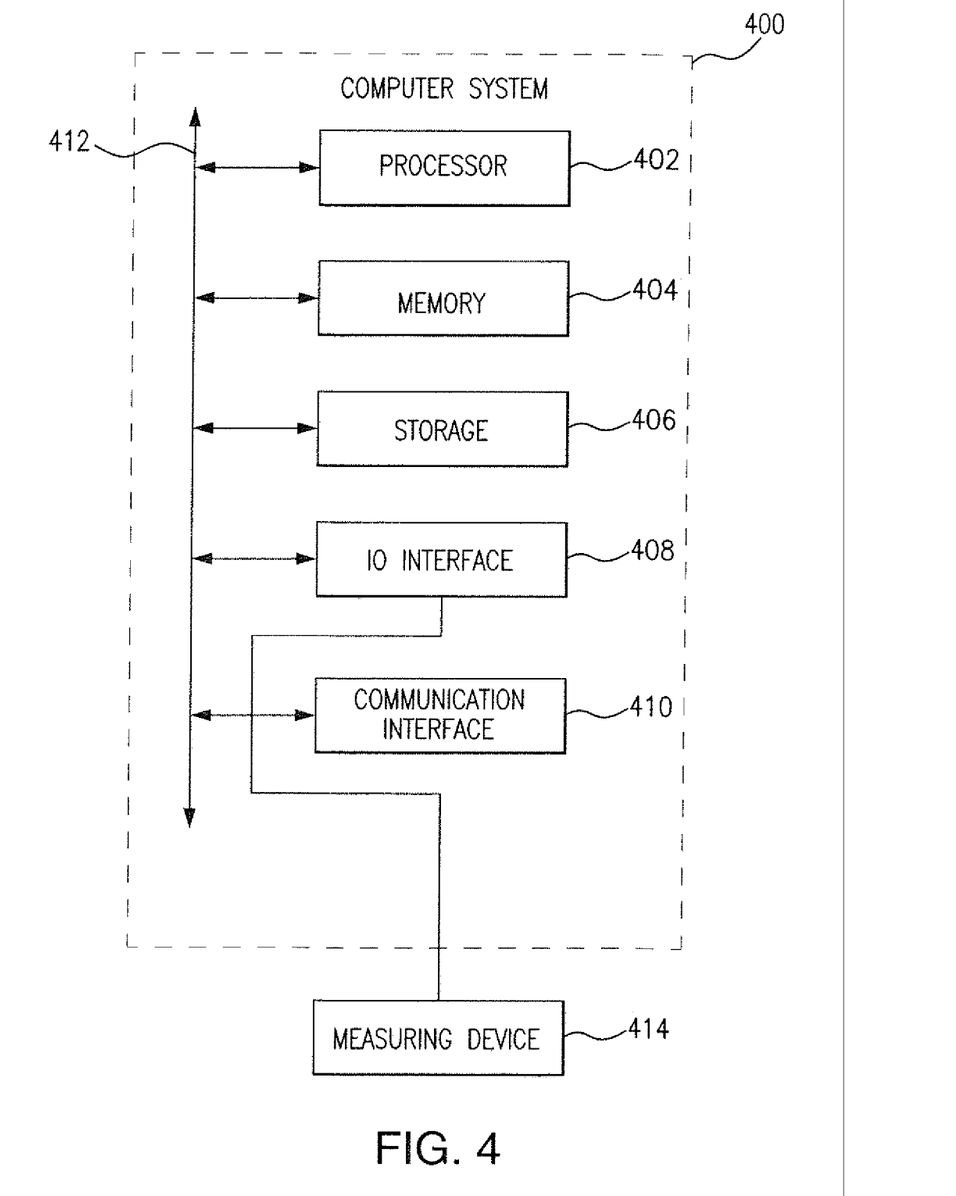
FIG. 4 is a diagram illustrating an exemplary computer system according to the disclosed subject matter.

As described above in connection with certain embodiments, a computer system 400 is provided to perform, among other features, storing of information to be encoded in the material and generating a binary number based on the information to be encoded, which can be read by measuring device 414. In these embodiments, the computer system 400 plays a significant role in permitting the method to provide material tracing. For example, the presence of the computer system 400 provides a determination of an amount of the tracer elements to be incorporated into the material corresponding to the binary number and can decode the binary number read by the measuring device to obtain information associated with the material.

FIG. 4 illustrates an example computer system 400. In some embodiments, one or more computer systems 400 perform one or more steps of one or more methods described or illustrated herein. In some embodiments, one or more computer systems 400 provide functionality described or illustrated herein. In some embodiments, software running on one or more computer systems 400 performs one or more steps of one or more methods described or illustrated herein or provides functionality described or illustrated herein. Some embodiments include one or more portions of one or more computer systems 400. Herein, reference to a computer system may encompass a computing device, and vice versa, where appropriate. Moreover, reference to a computer system may encompass one or more computer systems, where appropriate.

This disclosure contemplates any suitable number of computer systems 400. This disclosure contemplates computer system 400 taking any suitable physical form. As example and not by way of limitation, computer system 400 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, a tablet computer system, or a combination of two or more of these. Where appropriate, computer system 400 may include one or more computer systems 400; be unitary or distributed; span multiple locations; span multiple machines; span multiple data centers; or reside in a cloud, which may include one or more cloud components in one or more networks. Where appropriate, one or more computer systems 400 may perform without substantial spatial or temporal limitation one or more steps of one or more methods described or illustrated herein. As an example and not by way of limitation, one or more computer systems 400 may perform in real time or in batch mode one or more steps of one or more methods described or illustrated herein. One or more computer systems 400 may perform at different times or at different locations one or more steps of one or more methods described or illustrated herein, where appropriate.

In some embodiments, computer system 400 includes a processor 402, memory 404, storage 406, an input/output (I/O) interface 408, a communication interface 410, and a bus 412. Although this disclosure describes and illustrates a some computer system having a some number of some components in a some arrangement, this disclosure contemplates any suitable computer system having any suitable number of any suitable components in any suitable arrangement.

In some embodiments, processor 402 includes hardware for executing instructions, such as those making up a computer program. As an example and not by way of limitation, to execute instructions, processor 402 may retrieve (or fetch) the instructions from an internal register, an internal cache, memory 404, or storage 406; decode and execute them; and then write one or more results to an internal register, an internal cache, memory 404, or storage 406. In some embodiments, processor 402 may include one or more internal caches for data, instructions, or addresses. This disclosure contemplates processor 402 including any suitable number of any suitable internal caches, where appropriate. As an example and not by way of limitation, processor 402 may include one or more instruction caches, one or more data caches, and one or more translation lookaside buffers (TLBs). Instructions in the instruction caches may be copies of instructions in memory 404 or storage 406, and the instruction caches may speed up retrieval of those instructions by processor 402. Data in the data caches may be copies of data in memory 404 or storage 406 for instructions executing at processor 402 to operate on; the results of previous instructions executed at processor 402 for access by subsequent instructions executing at processor 402 or for writing to memory 404 or storage 406; or other suitable data. The data caches may speed up read or write operations by processor 402. The TLBs may speed up virtual-address translation for processor 402. In some embodiments, processor 402 may include one or more internal registers for data, instructions, or addresses. This disclosure contemplates processor 402 including any suitable number of any suitable internal registers, where appropriate. Where appropriate, processor 402 may include one or more arithmetic logic units (ALUs); be a multi-core processor; or include one or more processors 402. Although this disclosure describes and illustrates a some processor, this disclosure contemplates any suitable processor.

In some embodiments, memory 404 includes main memory for storing instructions for processor 402 to execute or data for processor 402 to operate on. As an example and not by way of limitation, computer system 400 may load instructions from storage 406 or another source (such as, for example, another computer system 400) to memory 404. Processor 402 may then load the instructions from memory 404 to an internal register or internal cache. To execute the instructions, processor 402 may retrieve the instructions from the internal register or internal cache and decode them. During or after execution of the instructions, processor 402 may write one or more results (which may be intermediate or final results) to the internal register or internal cache. Processor 402 may then write one or more of those results to memory 404. In some embodiments, processor 402 executes only instructions in one or more internal registers or internal caches or in memory 404 (as opposed to storage 406 or elsewhere) and operates only on data in one or more internal registers or internal caches or in memory 404 (as opposed to storage 406 or elsewhere). One or more memory buses (which may each include an address bus and a data bus) may couple processor 402 to memory 404. Bus 412 may include one or more memory buses, as described below. In some embodiments, one or more memory management units (MMUs) reside between processor 402 and memory 404 and facilitate accesses to memory 404 requested by processor 402. In some embodiments, memory 404 includes random access memory (RAM). This RAM may be volatile memory, where appropriate. Where appropriate, this RAM may be dynamic RAM (DRAM) or static RAM (SRAM). Moreover, where appropriate, this RAM may be single-ported or multi-ported RAM. This disclosure contemplates any suitable RAM. Memory 404 may include one or more memories 404, where appropriate. Although this disclosure describes and illustrates some memory, this disclosure contemplates any suitable memory.

In some embodiments, storage 406 includes mass storage for data or instructions. As an example and not by way of limitation, storage 406 may include a hard disk drive (HDD), a floppy disk drive, flash memory, an optical disc, a magneto-optical disc, magnetic tape, or a Universal Serial Bus (USB) drive or a combination of two or more of these. Storage 406 may include removable or non-removable (or fixed) media, where appropriate. Storage 406 may be internal or external to computer system 400, where appropriate. In some embodiments, storage 406 is non-volatile, solid-state memory. In some embodiments, storage 406 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. This disclosure contemplates mass storage 406 taking any suitable physical form. Storage 406 may include one or more storage control units facilitating communication between processor 402 and storage 406, where appropriate. Where appropriate, storage 406 may include one or more storages 406. Although this disclosure describes and illustrates some storage, this disclosure contemplates any suitable storage.

In some embodiments, I/O interface 408 includes hardware, software, or both, providing one or more interfaces for communication between computer system 400 and one or more I/O devices. Computer system 400 may include one or more of these I/O devices, where appropriate. One or more of these I/O devices may enable communication between a person and computer system 400. As an example and not by way of limitation, an I/O device may include a keyboard, keypad, microphone, monitor, mouse, printer, scanner, speaker, still camera, stylus, tablet, touch screen, trackball, video camera, another suitable I/O device or a combination of two or more of these. An I/O device can further include one or more sensors, such as measuring device 414, which as described above, can include a mass spectrometer, UV spectrometer, gamma spectrometer or any other suitable device for measuring amounts of the tracer materials, as described above. This disclosure contemplates any suitable I/O devices and any suitable I/O interfaces 408 for them. Where appropriate, I/O interface 408 may include one or more device or software drivers enabling processor 402 to drive one or more of these I/O devices. I/O interface 408 may include one or more I/O interfaces 408, where appropriate. Although this disclosure describes and illustrates a some I/O interface, this disclosure contemplates any suitable I/O interface.

In some embodiments, communication interface 410 includes hardware, software, or both providing one or more interfaces for communication (such as, for example, packet-based communication) between computer system 400 and one or more other computer systems 400 or one or more networks. As an example and not by way of limitation, communication interface 410 may include a network interface controller (NIC) or network adapter for communicating with an Ethernet or other wire-based network or a wireless NIC (WNIC) or wireless adapter for communicating with a wireless network, such as a WI-FI network. This disclosure contemplates any suitable network and any suitable communication interface 410 for it. As an example and not by way of limitation, computer system 400 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, computer system 400 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination of two or more of these. Computer system 400 may include any suitable communication interface 410 for any of these networks, where appropriate. Communication interface 410 may include one or more communication interfaces 410, where appropriate. Although this disclosure describes and illustrates a some communication interface, this disclosure contemplates any suitable communication interface.

In some embodiments, bus 412 includes hardware, software, or both coupling components of computer system 400 to each other. As an example and not by way of limitation, bus 412 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination of two or more of these. Bus 412 may include one or more buses 412, where appropriate. Although this disclosure describes and illustrates a some bus, this disclosure contemplates any suitable bus or interconnect.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

While the disclosed subject matter is described herein in terms of certain exemplary embodiments, those skilled in the art will recognize that various modifications and improvements can be made to the disclosed subject matter without departing from the scope thereof.

The foregoing merely illustrates the principles of the disclosed subject matter. Various modifications and alterations to the described embodiments will be apparent to those skilled in the art in view of the teachings herein. It will be appreciated that those skilled in the art will be able to devise numerous modifications which, although not explicitly described herein, embody its principles and are thus within its spirit and scope.

What is claimed is:

1. A method for encoding information in a material using a material tracing system in communication with a computer readable storage medium, comprising:
   storing, by the material tracing system in the computer readable storage medium, information to be encoded in the material;
   generating, by the material tracing system, a binary number based on the information;
   determining, by the material tracing system, an amount of at least one tracer to be incorporated into the material corresponding to the binary number, wherein the at least one tracer comprises one or more stable elements and/or non-radioactive elements that become radioactive upon activation;
   activating the one or more non-radioactive elements, if any, and
   incorporating the determined amount of the at least one tracer into the material.

2. The method of claim 1, wherein the at least one tracer comprises a plurality of trace elements, each trace element corresponding to one of a plurality of bits of the binary number, the method further comprising arranging the plurality of trace elements in an order corresponding to the order of the plurality of bits of the binary number.

3. The method of claim 2, wherein the amount of each of the plurality of trace elements comprises a first amount corresponding to a '1' bit of the binary number or a second amount corresponding to a '0' bit of the binary number, and determining the amount of the at least one tracer comprises, for each trace element, determining whether to incorporate the first amount of the trace element or the second amount of the trace element corresponding to the binary number.

4. The method of claim 1, wherein the at least one tracer comprises one or more radioactive elements.

5. The method of claim 4, wherein a total radioactivity of the one or more radioactive elements is less than or equal to 0.4 counts per second.

6. The method of claim 1, wherein activating the one or more elements comprises applying neutron irradiation to the one or more elements.

7. The method of claim 1, wherein the information comprises one or more of an age, purity, manufacturer, marking or serial number of the material.

8. The method of claim 1, wherein the binary number comprises a 64-bit binary number and the at least one tracer comprises 64 trace elements, each trace element corresponding to a bit of the 64-bit binary number.

9. A method for decoding information encoded in a material with at least one tracer incorporated into the material, the method comprising:
measuring an amount of the at least one tracer using a measuring device, wherein the at least one tracer comprises one or more stable elements and/or non-radioactive elements that become radioactive upon activation,
activating the one or more non-radioactive elements, if any;
determining a binary number corresponding to the measured at least one tracer based, at least in part, on the measured amount of the at least one tracer; and
decoding the binary number to obtain information associated with the material.

10. The method of claim 9, wherein the at least one tracer comprises a plurality of trace elements, each trace element corresponding to one of a plurality of bits of the binary number, the method further comprising obtaining an order of the plurality of trace elements corresponding to the order of the plurality of bits of the binary number.

11. The method of claim 10, wherein measuring an amount of the at least one tracer comprises measuring an amount of each trace element, the measured amount of each trace element comprising a first amount corresponding to a '1' bit of the binary number or a second amount corresponding to a '0' bit of the binary number.

12. The method of claim 9, wherein the at least one tracer comprises one or more stable elements, and measuring the amount of the at least one tracer comprises measuring the one or more stable elements using a mass spectrometer or a UV-visible spectrometer.

13. The method of claim 9, wherein the at least one tracer comprises one or more radioactive elements, and measuring the amount of the at least one tracer comprises measuring the one or more radioactive elements using a gamma spectrometer.

14. The method of claim 9, wherein the at least one tracer comprises one or more non-radioactive elements that becomes radioactive upon activation, and measuring the amount of the at least one tracer comprises activating the one or more non-radioactive elements by neutron irradiation.

15. The method of claim 9, wherein the information comprises one or more of an age, purity, manufacturer, marking or serial number of the material.

16. The method of claim 9, wherein the binary number comprises a 64-bit binary number and the at least one tracer comprises 64 trace elements, each trace element corresponding to a bit of the 64-bit binary number.

17. A material tracing system, comprising:
one or more processors; and
one or more computer readable storage media embodying software that is configured when executed by one or more of the processors to:
store, in the computer readable storage medium, information to be encoded in the material;
generate a binary number corresponding to the information; and
determine an amount of at least one tracer to be incorporated into the material corresponding to the binary number, wherein the at least one tracer comprises one or more stable elements and/or non-radioactive elements that become radioactive upon activation;
activate the one or more non-radioactive elements, if any, and
a measuring device in communication with the computer readable storage medium configured to:
measure the amount of the at least one tracer in the material;
determine the binary number corresponding to the measured at least one tracer based, at least in part, on the measured amount of the at least one tracer; and
obtain the information from the computer readable storage medium corresponding to the binary number.

18. The system of claim 17, further comprising a pellet fabricator coupled to the one or more processors and configured to form a pellet having the determined amount of the at least one tracer to be incorporated into the material.

19. The system of claim 17, further comprising a trace element activator configured to activate one or more inactive trace elements.

* * * * *